United States Patent [19]

Nambu et al.

[11] Patent Number: 4,774,957
[45] Date of Patent: Oct. 4, 1988

[54] MATERIAL FOR DIAGNOSIS BY NUCLEAR MAGNETIC RESONANCE IMAGING

[75] Inventors: Masao Nambu; Hitoshi Goshima, both of Yokohama; Isamu Mano, Kashiwa, all of Japan

[73] Assignees: Kabushiki Kaisha Toshiba, Kawasaki; Nippon Oil Co. Ltd., Tokyo, both of Japan

[21] Appl. No.: 97,339

[22] Filed: Sep. 11, 1987

Related U.S. Application Data

[63] Continuation of Ser. No. 855,109, Apr. 23, 1986, abandoned.

[30] Foreign Application Priority Data

Apr. 26, 1985 [JP] Japan .................................. 60-88707
Apr. 26, 1985 [JP] Japan .................................. 60-88708

[51] Int. Cl.⁴ ...................... A61B 5/05; G01R 33/20; C08L 29/04; B29C 39/02
[52] U.S. Cl. .................................. 128/653; 156/242; 264/28; 264/101; 264/154; 264/271.1; 264/331.15; 324/308; 324/309; 428/419; 524/557; 525/56
[58] Field of Search ...................... 264/28, 101, 331.18, 264/331.21, 331.15, 154, 271.1; 324/308, 309, 307; 128/653; 428/419; 524/557; 525/56; 523/309

[56] References Cited

U.S. PATENT DOCUMENTS

| | | | |
|---|---|---|---|
| 4,148,689 | 4/1979 | Hino et al. | 435/182 |
| 4,301,411 | 11/1981 | Wardell et al. | 324/308 X |
| 4,472,542 | 9/1984 | Nambu | 523/309 |
| 4,528,510 | 7/1985 | Loeffler et al. | 324/309 |
| 4,583,538 | 4/1986 | Onik et al. | 128/653 X |
| 4,591,789 | 5/1986 | Glover et al. | 324/307 |
| 4,613,819 | 9/1986 | Chui | 324/308 |
| 4,618,826 | 10/1986 | Smith et al. | 324/308 |
| 4,625,168 | 11/1986 | Meyer et al. | 324/308 X |
| 4,635,643 | 1/1987 | Brown | 128/653 |
| 4,637,929 | 1/1987 | Quay | 128/653 X |
| 4,639,365 | 1/1987 | Sherry | 128/653 X |
| 4,644,276 | 2/1987 | Sierocuk et al. | 324/307 |
| 4,654,593 | 3/1987 | Ackerman | 324/307 |
| 4,665,364 | 5/1987 | Hanawa | 324/308 X |
| 4,684,889 | 8/1987 | Yamaguchi et al. | 324/308 |
| 4,687,658 | 8/1987 | Quay | 128/653 X |
| 4,687,659 | 8/1987 | Quay | 128/653 X |
| 4,701,705 | 10/1987 | Rollwitz | 324/308 X |
| 4,710,715 | 12/1987 | Mee et al. | 324/307 |
| 4,713,614 | 12/1987 | Hoshino et al. | 324/307 |
| 4,716,368 | 12/1987 | Haacke | 324/308 X |
| 4,719,098 | 1/1988 | Weinmann et al. | 128/653 X |

FOREIGN PATENT DOCUMENTS

| | | | |
|---|---|---|---|
| 204320 | 12/1986 | European Pat. Off. | 324/308 |
| 49-28639 | 3/1974 | Japan | 525/56 |
| 56-36538 | 4/1981 | Japan | 525/56 |
| 57-190072 | 11/1982 | Japan | 524/557 |
| 2157832A | 10/1985 | United Kingdom | 324/308 |

OTHER PUBLICATIONS

Damadian, Raymond; Lawrence Minkoff; Michael Goldsmith and Jason A. Koutcher "Field-Focusing Nuclear Magnetic Resonance (Fonar)" in *Naturwissenschaften*, vol. 65, No. 5, May 1978, pp. 250–252.

Frahm, J.; K. D. Merboldt; W. Hanicke; and A. Haase "Stimulated Echo Imaging" in *Journal of Magnetic Resonance*, 64, 81–93 (1985).

Polymer Applications 32: 523 (1983).

*Primary Examiner*—Philip Anderson
*Attorney, Agent, or Firm*—Keil & Weinkauf

[57] ABSTRACT

A material for diagnosis by nuclear magnetic resonance imaging is provided. The material comprises a hydrogel having a high water content. The hydrogel is prepared by the steps of casting an aqueous polyvinyl alcohol solution into a mold, cooling the case aqueous solution to obtain a cooled frozen mass and thawing the cooled frozen mass. The cooling and thawing steps may be repeated up to eight cycles. The hydrogel is also prepared by subjecting the cooled frozen mass to a partial dehydration step in vacuum.

18 Claims, 1 Drawing Sheet

MATERIAL FOR DIAGNOSIS BY NUCLEAR MAGNETIC RESONANCE IMAGING

This application is a continuation of application Ser. No. 855,109, filed on Apr. 23, 1986 and now abandoned.

BACKGROUND OF THE INVENTION

1. Filed of the Invention;

The present invention relates to a material used for diagnosis by nuclear magnetic resonance imaging, and particularly to a material which may be used for the preparation of models equivalent to living tissue, such as simulating images, phantoms or reference materials, required in maintenance, inspection, servicing and appraisal of a system used for diagnosis by nuclear magnetic resonance (NMR) imaging and required also in analysis and study of the images obtained by the NMR diagnosis It will be noted here that the expression "diagnosis by nuclear magnetic resonance" or "NMR diagnosis" used throughout the specification and appended claims means the diagnosis of a certain diseased site by the analysis of the NMR image of the diseased site. The material provided by the present invention may also be used for the preparation of a skin marker which is applied on a certain position of the patient body in the practice of NMR tomography wherein the location of the diseased site should be determined, while a certain point or position of the surface of the patient body is taken as a reference location, prior to the commencement of the radiotherapy or surgical treatment.

2. Related Art Statement

The method for the diagnosis of an internal site, for instance, to have an information concerning a certain diseased site or a condition of blood stream, is generally referred to as the NMR image diagnosis method, the NMR tomographical diagnosis method, the NMR imaging method, MRI (magnetic resonance imaging) method, the MMR (medical magnetic resonance) method, the MNI (multi-nuclear imaging) method and he NMR-CT (computerized or computer assisted tomography) method. In such a method, a living body is placed in a static magnetic field and applied with a radio-frequency wave (having a high frequency) corresponding to the resonance wave length with the atomic nucleus of hydrogen or proton to excite protons in the living tissue, and then the magnetic information generated from the thus excited atomic nuclei are detected as the output signals to form an image by such output information. Such an image includes the nuclear magnetic information concerning the concentration of protons contained in the living tissue (which gives an information concerning the water content in the living tissue), those concerning the spin-lattice (longitudinal) relaxation time ($T_1$) and those concerning the spin-spin (transverse) relaxation time ($T_2$). By analysing the image, the condition of the diseased site may be distinguished, and the distribution of the blood stream velocity in the living tissue may be imaged. The NMR imaging method is expected as a novel tool for the early stage diagnosis of a variety of diseases, since it is superior over or overcoming the demerits of the known X-ray tomography, DSA (digital substraction angiography), PET or PE-CT (positron emission tomography) and US (ultrasonic method) for the reasons that any desired cross section of a living tissue can be imaged without trepassing internally of the living tissue, without being disturbed by the bones or air in the respiratory organs, and without any apprehension of exposure by a radioactive isotope or X-ray. However, the conventional system used for the NMR diagnosis is inferior in operational stability when compared with the stabilities of the systems used for the X-ray-CT and PE-CT methods. (In this connection, reference should be made to Hiroki Kawaguchi, "SHIMAZU HYORON", 41, 137 (1984).) In practice of the NMR imaging, the system used therefor must always be paid with continuous care as to its maintenance, inspection, servicing, adjustment and appraisal of the performance characteristics.

In general, the device for reading out an information and the display device incorporated in the NMR system are computerized, and it has been pointed out that "there is a grave tendency that exceedingly many chemists apt to accept the displayed data as accurate analytical results without taking what has been done in the system into account." In the NMR system for diagnosis, the control system, the manual for operations and the mode of imaging have not been standardized, often leading to difficulty in study and analysis of the image. Under such circumstances, certain erroneous diagnoses have been specifically pointed out and there is earnest demand for the search and establishment of a standard probe used for inspecting the operational condition of the system (E. L.. Madsen, "Mag. Res. Imag.", 1, 135 (1982)).

It is desired that an NMR system should be placed at a location in a building constructed of wooden and plastics materials and isolated from the hospital, ideally pipes for city water, gases and drainage conduits being made of non-magnetic materials, such as synthetic resins, and a fluorescence lamp should not be used in the building. In the general practical application, such systems are installed within hospital buildings while being shielded from the neighbouring magnetic materials. However, it is necessary that the system should be separated by a distance of more than 10 meters from an elevator, roadway, underground railway and similar equipment, and it is also necessary that all of the neighbouring magnetic wave generating sources including television, magnetic tapes and electric lead cables should be shielded. However, there is often a case where such necessary condition is not satisfied. It will thus be understood that the operational conditions for satisfactory functional effect of the NMR system depends seriously on the maintenance, control and adjustemnt thereof, so that the adverse influences by the iron base materials in the building structure and/or surrounding substances should be amended by the provision of a symmetrical coil. However, significant difficulties are encountered in amendment of the influences due to magnetic field established by radio frequency waves or plate-shape magnetic wave sources. In addition, since the system cannot be assembled pecisely in accordance with the theory and design thereof, similarly to general precise mechanical instruments, it is frequently pointed out the uneven orientation of the static magnetic field in the transverse direction, and it is hard to amend such an uneven orientation of the magnetic field. Although it is convenient from the economical standpoint of view to lessen the magnetic field, in order to improve the uniformity of the static magnetic field, in order to improve the uniformity of the static magnetic field, it is meaningless to provide an NMR system for handling a small sample or test specimen when it is intended that the system is used for the diagnosis of a human body. It should be appreciated that a large scale magnet used for the diagnosis of a human body is accompanied with various imperfections which are not corrected or amended to give satisfactory data since no standard therefor has not yet been established at the present day.

In operation of the system, there are many problems which should be born in mind of the operator or the analyst. For example, the level of the radio frequency wave and the pulse interval should be properly selected, and the scanning speed should be pertinently set not to reduce the resolution power of the system, depending on the conditions of the disease. Furthermore, the NMR signals depend on the specific type of system used and on the intensity of the static magnetic field, and the conversion factor between different systems can not be determined monistically, as reported by I. Young, "Electronics & Power", 1984, March, 205. Moreover, even when the same system is used, the $T_1$ and $T_2$ (image signals) vary in response to the pulse interval $(T_r)$, the delay time $(T_d)$ and the echo time $(T_e)$. However, the photographing condition for imaging cannot be set monistically to a certain condition. In detail, the difference (i.e. the contrast between the image of normal tissue and that of diseased site) in the NMR signal induced by the change due to a morbid state is to be discriminated by the NMR diagnosis. However, since more than an hour is expended for individual imaging by calculation of the NMR signals (proton density $\rho$, $T_2$) and special value can not always be expected by such individual imaging, it is a common practice to form an image including all of the above factors as a prompt measure. In such a case, rather than taking the aforementioned three factors equally into account, the endeavor is directed to the establishment of an image having clear contrast so as to have the maximum discremination ability for discriminating the diseased site by imaging the respective factors through the non-uniformly weighed addition (while adopting the trial-and-error method) in response to the condition of disease, the personal difference and the conditions of the surrounding tissues around the diseased site. (In this connection, reference should be made to G. Hansen et al., "Radiology", 136, 695 (1980); I. E. Crooks, "I.E.E.E. Trans. Nucl. Sci.", NS-27, 1239 (1980).) For these reasons, unitary display of the NMR signals is sacrificed to result in devoid of interchangeability between the images to induce problems in analysis of the images inevitably.

In consideration of the aforementioned status quo of the NMR imaging technology, it is a natural demand for a reference or control specimen for the objective appraisal, judgement on the maintenance, control, adjustment operational and performance conditions and for the analysis of the formed images. Examples of the materials which have been already proposed as those which maybbe used for the preparation of reference specimen in the NMR imaging method, include tetramethylsilane, hexamethyldisiloxane, hexamethyldisilane, neopentane, DSS (sodium 2,2-dimethyl-2-silapentano-5-sulfonate) and sodium 2,3-tetradeuterium-3-trimethylsilylpropionate. Although these materials are conveniently used in the chemical analysis as the materials for preparing reference specimens used to measure the chemical shifts of the NMR informations, they are not suited for use as the materials for the reference specimen used to provide basic informations or factors (proton density $\rho$, $T_1$ and $T_2$) in the NMR diagnosis, at all.

In some cases, polymethyl methacrylate and a low density polyethylene have been used in an NMR system for the adjustment purpose. However, the polymethyl methacrylate is used merely for the inspection of the peak width of the chemical shift during the chemical analysis and the low density polyethylene is used only for the adjustment of the level of radio frequency wave. The both materials have no utility as the reference materials used for the adjustment operation when the system is used for obtaining NMR informations concerning a living body.

It has been proposed to use water, an aqueous solution of manganese sulfate, nickel chloride or copper chloride, and sulfuric acid, as the standard for inspection and adjustment of the system, since the NMR diagnosis is applied for the diagnosis of a substance (i.e. a living tissue) containing a large quantity of water. However, water is improper for a standard in the NMR analysis at all, since it is seriously affected by the changes in test conditions, such as temperature, trace amounts of impurities, e.g. dissolved oxygen, iron or nickel. On the other hand, it is extremely difficult to prepare a solution simulating NMR informations of a living tissue (water content, $T_1$ and $T_2$) by the use of any of the aforementioned solutions.

There are known in the art a variety of solids (gels) containing water and having a construction resembling living tissues, the examples being gelatin, agar, polyacrylamide, carrageenan, agarose, jam, boiled egg, KONNYAKU (devil's tongue), alginic acid gel and bean-curd. However, a material having a water content agreed with that of the internal organs of a living body (namely, having a water content of from about 70 to 85 wt. %) and having the $T_1$ and $T_2$ values agreed with those of the internal organs of a living body has not yet been known. Although continuous attempts are made to improve the process for the preparation of these hydrogels so as to bring the NMR signals $\rho$, $T_1$, $T_2$) thereof close to those of the living tissues by admixing some quantities of impurities, such attempts have not succeeded as will be described hereinbelow. It is also required that such a material must be suited for the provision of a living tissue model (phantom) having good performance characteristics, shape-retaining property or satisfactory moldability for simulating internal organs. However, a material satisfying all of the requirements, as mentioned above, has not yet been offered. For instance, a gelatin containing more than 70% of water is too weak and apt to be broken, and a gelatin containing 60 to 70% of water has an excessively high $T_1$ and $T_2$ values as compared to those of the living tissues. Chemical treatment of gelatin has been studied to eliminate the tendency of fluidization thereof at the room temperature and to improve the $T_1$ and $T_2$ values thereof. However, such efforts produced no valuable fruit, since there appeared uneven gelation during the step of cross-linking and solidifying the gelatin. Anyway, it is not expectable to bring the three factors, i.e the water content (70 to 85%), $T_1$ and $T_2$, close to those of the living tissues by the use of any gelatin composition. Although a polyacrylamide gel having a water content ranging from 70 to 85% may be prepared, such a gel has an exceedingly high $T_2$ value and is apt to lose uniform structure during the cross-linking polymerization (gelation) step. Further disadvantages of such a polyacrylamide gel are that the gel per se is too fragile to be easily broken and that the NMR signals vary with the lapse of time.

Other known materials include bean-curd, carrageenan, alginic acid, agar, agarose, boiled egg, poly(2-hydroxyethyl methacrylate) gel, Curdlan (I. Maeda et al., "Agr. Biol. Chem.", 31, 1184 (1967)), carboxymethyl cellulose (CMC), acrylonitrile-stach graft gel (E. B. Bagley et al., "Ind. Eng. Chem. Prod. Res. Dev.", 14, 105 (1975)), xanthane gum, Locust Bean Gum, tragacanth gum, furcellaran, methyl cellulose, casein, albumin, fucoidin, triethanolamine alginate, tamarind gum, karaya gum, gatti gum and jam (such as pectin gel). However, all of these materials are too weak as the materials used for constructing models, and in addition water content of each of these materials is limited so that both of $T_1$ and $T_2$ thereof cannot be agreed with those of living tissues. Although the KONNYAKU and poly(N-vinylpyrrolidone) have tentatively satisfactory shape-retaining property and moldability, the water content of the former is too large with extremely high $T_1$ and $T_2$ values, and the latter has an adequate water content but is too high in $T_1$ and $T_2$ values. Even if an adjusting agent, such as nickel, manganese, copper or graphite, is added to poly(N-vinylpyrrolidone), both of the $T_1$ and $T_2$ values thereof cannot be brought to the values equivalent to those of living tissues.

Because of the fact that any of the known materials (chemical substances) have many demerits, as described above, a fresh tissue of an animal has been used reluctantly as the control material in practice. However, such an animal-originated material is deteriorated significantly with the lapse of time even when stored in a cold place, as reported by R. V. Damadian, U.S. Pat. No. 3,789,832 (1974), and significant differences are found between the samples picked up from individual animals of the same species. Under such circumstances, it should be reasonable and well-grounded to accept the opinion, which has been repeatedly pointed out, for example, by E. L. Madsen, "Mag. Res. Imag.", 1, 135 (1982), that it is necessary to find out a water-containing material (for phantom) which is not originated from a living body (namely a chemical substance) and repeatedly usable for a long time while having substantially equivalent NMR informations ($\rho$, $T_1$, $T_2$) and being improved in shape-retaining property and satisfactory moldability.

It is also necessary to learn the precise steriographical position of a certain diseased site or to learn the precise distance from certain standard locations on the surface of a patient body prior to trepass internally of the patient for the purpose of examination or medical treatment, in order to increase the effect of surgical treatment and to minimize damages of normal tissues surrounding the diseased site by the surgical treatment. One example of such diagnosis methods is the so-called NMR-CT method (nuclear magnetic resonance crossectional tomography). Although many internal organs and various diseased sites may be clearly displayed by the NMR-CT method without trepassing internally of the living body, the locations thereof, particularly the relative positioning or distance of each diseased site from a ceratin location on the surface of the patient body, are not clarified by the NMR-CT method.

In a medical treatment by radiography or various surgical operations or treatments, the living tissue at a certain diseased site in a living body is intended to be destroyed or resected through another specific position on the surface or skin of the body, and thus it is essential to learn the precise interrelation between the specific position on the skin and the certain diseased site internally of the living body by preliminary measurement.

In a case where a diseased site, such as hematoma or tumour, is occasionally present on the skin surface, both of the disease on the skin and the diseased site within the living body can be imaged clearly and concurrently. However, such a case is rare and unexpectable.

It is, therefore, the most convenient measure to apply some substance which emits a clear NMR signal different from the signal emitted from a normal skin tissue on a certain location of the skin (on a normal skin of the living body) across the cross section of the diseased site within the body, whereby the specific location on the surface of the body is imaged on the NMR cross sectional picture together with the image of the diseased site in the body. However, it is not easy to provide a substance (such a substance being referred to as "skin marker" in the art) which always satisfies the aforementioned requirement under the operation condition (within the range of operation) for the NMR diagnosis. Water (pure water) is the first substance which should be called to mind as a material suitably used for this purpose. Pure water emits a more intensive proton signal as compared with that emitted from the skin which contains 51 to 69% of water, with the longitudinal relaxation times ($T_1$) and especially transverse relaxation time ($T_2$) are prolonged, and has an advantage that it is not harmful to the skin. However, pure water has no shape-retaining property when put on the skin. This problem may be tentatively obviated by applying a pouch filled with water on the skin surface. However, it is desirous that a marker having initially an arbitrary shape and dimensions be applied on the surface of the living body, followed by stepwise cutting of the peripheral portions of the marker during the sequential operations of forming cross sectional images thereof together with the formation of images of the diseased site so that the shape and dimensions of the marker are brought closer to those of the diseased site to form an image of the diseased site (having certain shape and dimensions) on the skin surface. Since the pouch containing water cannot be cut, it does not satisfy such requirement. There have been known some materials which contain large quantities of water to emit NMR signals close to that emitted from water and may be cut to have shapes and dimensions which agree with those of the diseased site, the examples being gels of jelly, jam, agar, carrageenan, carboxymethyl cellulose, polyvinyl alcohol complexes of boric acid, bean-curd, alginic acid, agarose, curdlan, acrylonitrile-starch graft polymer, xanthane gum, Locust Bean gum, tragacanth gum, furcellaran, methyl cellulose, fucoidin, tamarind gum, karaya gum and gatti gum. However, all of these gels are poor in mechanical strength, and some of them have no shape-retaining properties so as to be unsuited for adhesion and fixation on a certain location of the skin surface.

Although a Congo Red complex of polyvinyl alcohol has a high water content and elasticity resembling that of a soft rubber, it is not preferred since it is harmful to living tissues as disclosed by S. Niedermeier, "Graefes Archiv Für Ophthalmol.", 161 547 (1960), C. L. Schepens et al., "Arch. Ophthalmol.", 64, 868 (1960), W. C. Everett, "Klin. Monatsbl. Augenheilkd.", 141 764 (1962) and Ei Sakaue, "Jap. J. of Clinical Ophthalmology" 18, (1), 7 (1964). The polyacrylamide gel is also harmful to a living body and has another disadvantage that it is mechanically fragile.

KONNYAKU has a shape-retainig property notwithstanding the fact that it contains about 98% of water and emits and NMR signal closely resembling that of water, and may be cut freely. However, KONNYAKU is not suited for rapid and simplified use in response to the need in actual clinical treatment, since it has a problem in storage due to the fact that it tends to be collapsed or fluidized and being suffered from serious syneresis, contraction and deformation unless it is stored while being dipped in a vessel filled with a strong alkali solution (pH 11 to 12) containing an antiseptic agent.

OBJECTS AND SUMMARY OF THE INVENTION

A primary object of this invention is to provide a material used for diagnosis by nuclear magnetic resonance (NMR) imaging, which material is not originated from a living body, yet has NMR properties ($\rho$, $T_1$, $T_2$) equivalent and equi-qualitive to those of a living tissue stably, is improved in moldability and machinability, and has satisfactory shape-retaining property.

Another object of this invention is to provide a material used for diagnosis by nuclear magnetic resonance (NMR) imaging, which material can be molded to have a desired shape and stored to retain its original shape even at 37° C. notwithstanding the fact that it contains a large amount of water.

A further object of this invention is to provide a material used for diagnosis by nuclear magnetic resonance (NMR) imaging, which material may be added with a large quantity of lipid to prepare a phantom simulating a living fatty tissue in which a small amount of water is contained.

A further object of this invention is to provide a material used for diagnosis by nuclear magnetic resonance (NMR) imaging, from which prepared is a phantom satisfying the factors for a model equivalent to a living organ to have nuclear magnetic informations concerning air, stagnant liquid or blood, while being provided with a vacant cavity or a cavity for storing water simulating the trachea, lung, blood vessel, stomach, bladder, ureter or urethra internally thereof.

A still further object of this invention is to provide a material used for diagnosis by nuclear magnetic resonance (NMR) imaging, from which prepared is a harmless marker to be applied on the surface of skin, the marker having stable NMR properties (water content, $T_1$, $T_2$) different from those of the skin surface of a living body and having satisfactoty shape-retaining property and yet having a capability of being cut to have any desired shape.

Yet a further object of this invention is to provide a material used for diagnosis by nuclear magnetic resonance (NMR) imaging, from which prepared is a marker to be applied on the surface of skin, the marker adhering and being fixed at any location on the surface of a living body.

The above and other objects of this invention will become apparent from the following detailed description.

The material for diagnosis by nuclear magnetic resonance imaging, provided in accordeance with the present invention, comprises a hydrogel having a high water content and being prepared by a process comprising a casting step of casting an aqueous solution containing more than 8 wt. % and not more than 50 wt. % of a polyvinyl alcohol having a degree of hydrolysis of not less than 98 mol % and an average polymerization degree of not less than 1000 into a mold having desired shape and dimensions, a freezing step of cooling the cast aqueous solution to a temperature of not higher than—(-minus) 10° C. to obtain a cooled frozen mass, and a thawing step of thawing the cooled frozen mass, the freezing step and the thawing step being repeated up to eight cycles.

According to a further aspect of the invention, provided is a material for diagnosis by nuclear magnetic resonance imaging, which comprises a hydrogel having a high water content and being prepared by a process comprising a casting step of casting an aqueous solution containing more than 8 wt. % and not more than 50 wt. % of a polyvinyl alcohol having a degree of hydrolysis of not less than 98 mol % and an average polymerization degree of not less than 1000 into a mold having desired shape and dimensions, a freezing step of cooling the cast aqueous solution to a temperature of not higher than—(minus) 10° C. to obtain a cooled frozen mass, and a partial dehydration step of dehydrating the cooled mass in vacuum until the percentage dehydration rate reaches not less than 3 wt. %.

DESCRIPTION OF THE INVENTION

The present invention will be described more specifically hereinbelow.

The polyvinyl alcohol used in the present invention should have a degree of hydrolysis of not less than 98 mol %, preferably not less than 98.5%. It is also essential that the polyvinyl alcohol has a degree of polymerization of not less than 1,000.

In the present invention, an aqueous solution containing the aforementioned polyvinyl alcohol is prepared at the first step. The content of the polyvinyl alcohol in the solution should be in the range of more than 8 wt. % and not more than 50 wt. %, preferably from 9 to 45 wt. %. Particularly when the material of the invention is used to form a skin marker for the NMR diagnosis, the content of polyvinyl alcohol in the aquesous solution may preferably be in the range of more than 8 wt. % and not more than 20 wt. %, more preferably from 9 to 15 wt. %.

In the next step of the process of the invention, the aqueous solution of polyvinyl alcohol, as described above and defined in the appended claims, is cast into a mold for molding a desired shape including circular, rectangular and elliptical plates or shapes and a strip-like plate, for the case where a phantom or a skin marker is formed from the material of the invention. The phantom may also be molded to have spherical, annular, cylindrical and tubular shapes, as desired. Then, the molded mass is cooled to be frozen, and the frozen mass is thawed to prepare a hydrogel having high water content, and the hydrogel is offered to the aimed use, according to the invention. The hydrogel having a high water content, provided by the invention, may be subjected to repeated freezing and thawing cycles of up to 8 times or cycles, when it is desired to prepare a material for the NMR diagnosis having particularly high mechanical strength. It is recommended, from the economical standpoint of view, that the freezing and thawing cycles are repeated from 2 to 8 times in consideration of the fact that the advantageous increase in hardness of the hydrogel with the increase in repeated cyclic treatments is saturated substantially by the 8 time repeated cycles and the increase of hardness or strength of the hydrogel is not so high after ninth cycle. (In this connection, reference should be made to Masao Nambu, "Polymer Application", 32, 523 (1983).)

According to another aspect of the invention, the frozen mass may be partially dehydrated in vacuum after it is cooled to be frozen, in lieu of subjecting the same to the freezing and thawing steps. When a partial dehydration step effected in vacuum is adopted, the mechanical strength of the hydrogel is improved as the percentage dehydration rate is increased. It should be noted here that the wording "percentage dehydration rate" as used in this specification and claims is expressed by the percentage reduction of the weight of the cooled and solidified gel. However, it is not necessary to increase the percentage dehydration rate to an extremely high level to form a strong gel, and the percent dehydration rate should be not less than 3 wt. %, preferably in the range of not less than 3 wt. % and not more than 60 wt. %, more preferably not less than 3 wt. % and not more than 35 wt. % to improve the shape-retaining property and machinability of the resultant gel.

The partial dehydration in vacuum means that the hydrogel is dehydrated at some extent under a reduced pressure, and the level of reduced pressure is not particularly limited and ranges, for instance, not higher than 1 mmHg, preferably not higher than 0.1 mmHg and more preferably not higher than 0.08 mmHg. The mold is not particularly restricted as far as a molded product having a desired cylindrical, tubular, annular, strip shape, etc. is molded by the use thereof. The thickness (uniformity in thickess or thickness distribution) and the shape and dimensions of the molded product may be properly selected in compliance with the practical application in the NMR diagnosis.

The only material for forming a hydrogel, i.e. the gel forming ingredient, used in the present invention is the polyvinyl alcohol as defined in the claims. However, other ingredients or additives, which do not hinder the gelation of polyvinyl alcohol, may be present in the aqueous solution of the polyvinyl alcohol, the amount of the coexisting additives being, for example, controlled in the range of not more than one half in weight of the weight of the polyvinyl alcohol contained in the gel forming solution.

Examples of the additives which do not hinder gelation of the polyvinyl alcohol and may be contained in the gel forming solution are alcohols such as isopropyl alcohol, glycerin, propylene glycol and ethyl alcohol; proteins such as casein, gelatin and albumin; lipids such as lecithin, monostearin and tristearin; saccharides and polysaccharide such as glucose, agar and carrageenan; organic compounds such as butyl-p-hydroxybenzoate and phthalocyanine and flavanthrone; and inorganic compounds, inorganic salts and organic salts such as nickel salts, copper salts, manganese salts, iron salts, graphite, activated carbon, silica-alumina, zeolite and calcium silicate. One or more of these additives may be directly, or in the form of an aqueous solution or suspension, added in the aqueous solution of polyvinyl alcohol under agitation to be dispersed uniformly therein, and then the aqueous solution or dispersion may be subjected to the subsequent freezing and the other treatment steps.

According to the present invention, the water content of individual hydrogels may be arbitrarily varied to be agreed with the water contents of various living tissues for the provision of a variety of phantoms adapted for use in the NMR diagnosis. Hydrogels having water contents well suited for use as skin markers in the NMR diagnosis may also be prepared, according to the invention. The water content of a certain hydrogel depends on the preparation or composition of the aqueous solution or suspension of polyvinyl alcohol used in the initial step. When the aqueous solution or suspension of polyvinyl alcohol is subjected to partial dehydration step after it has been frozen, the water content of the resultant hydrogel may be determined by calculating the amount of removed water deprived at the partial dehydration step. The water content of a hydrogel which is prepared, without subjecting to partial dehydration, by simply freezing and thawing (or subjecting to repeated freezing and thawing cycles) may be easily calculated since the aqueous solution of polyvinyl alcohol used at the initial step has been gelled without removal of water therefrom.

Therefore, a certain phantom usable in the NMR diagnosis and prepared by the present invention has a predetermined water content set to simulate the water content of the specific living tissue, such as skin (Water Content: 51 to 69%), ureter (Water Content: 58%), Lig. nuchae (Water Content: 58%), Achilles tendon (Water Content: 63%), tongue (Water Content: 60 to 68%), prostate (Water Content: 69 to 76%), lens (Water Content: 67 to 70%), liver (Water Content: 73 to 77%), stomach (Water Content: 80%), pancreas (Water Content: 75%), small intestine (Water Content: 80%), skeletal muscles (Water Content: 79 to 80%), uterus (Water Content: 80%), and thymus (Water Content: 82%), bladder (Water Content: 82%). The phantoms prepared by the invention are characterized by the fact that they have the $T_1$ and $T_2$ values substantially agreed with those of the simulated living tissues. A phantom simulating a tissue enriched in lipid may be prepared by admixing a lipid in the initially prepared aqueous solution of polyvinyl alcohol followed by dispersing the same uniformly in the solution. For example, when it is desired to prepare a phantom simulating a fat tissue containing 40% of water, an equivalent amount of lecithin or tristearin or another similar lipid is dispersed in an aqueous solution of polyvinyl alcohol having a water content of 80%. In preparation of a phantom simulating a tissue having a higher fat content, a solid fat, such as monostearin or tristearin, is heated to be liquefied and then the liquefied fat is added to an aqueous solution of polyvinyl alcohol which has been heated to a temperature of not lower than 70° C. thereby to disperse the fat uniformly in the solution, prior to conducting the freezing step of the process of the invention, in order to preclude the fear that the shape-retaining property of the phantom (gel) is deteriorated due to the presence of the fat. Through the operations as described above, a phantom corresponding to a fat tissue containing 15 to 30% of water may be prepared, and the thus prepared phantom has $T_1$ and $T_2$ values substantially agreed with those of a fat tissue of a living body.

According to a further important feature of the invention, two or more phantoms which are differnt from each other in water content may be bonded or joined together to form a composite phantom. A cyanoacyrylate base adhesive may be used as the adhesive for preparing such a composite phantom, it is more convenient that an aqueous solution of polyvinyl alcohol having a desired water content is applied on the surfaces to be joined, and then the surfaces applied with the aqueous solution are joined, followed by additional freezing and thawing operations.

In a case where a skin marker is prepared from the material of the invention, it is recommended that the water content thereof is set to a level (not less than the range of from 56 to 74%) which is higher than the water content of the skin of a living body (normally ranging within 51 to 69%) by 5% or more, and more preferably the water content of the skin marker should be set to a value of not less than 80% to form a clear image.

In the present invention, a material used for the NMR diagnosis and having a pertinent shape may be molded by the use of a mold having a desired mold cavity. Alternatively, a gel having a certain desired shape is formed and then the gel may be cut by scissors or a sharp cutter to have a final desired shape. Moreover, a cylindrical bar or a round rod is embedded in the mold at the step of preparing a phantom which is used in te NMR diagnosis, or a hot iron rod having a circular section is thrusted into the solidified hydrogel to form a passage simulating a blood vessel within the phantom, whereby a phantom for flowing therethrough a water stream simulating the blood stream in a living body may be prepared.

On the other hand, a skin marker for the NMR diagnosis may have a shape or contour simulating a diseased site (or anticipated diseased site). In addition, a membrane or plate which covers a large skin area is prepared and a vacant hole or void area is scooped so that the void area may be used as the marked location.

A phantom made of the material for the NMR diagnosis, according to the invention, has $T_1$ and $T_2$ values substantially agreed with those of a living tissue, and thus satisfy the requirements concerning the NMR informations (water content, $T_1$, $T_2$) for forming a model equivalent to a living tissue; and it contains water which may be varied within a wide range of from 50 to 92 wt. % to cover the water contents of various living tissues which varies from 58 to 61% for the skin and Lig. nuchea to 78 to 82% for the liver and bladder.

On the other hand, a skin marker made of the material for the NMR diagnosis, according to the invention, has a water content of up to 80 to 92 wt. % to emit an NMR signal clearly different from that emitted from a skin of a living body containing 51 to 69% of water, so that a distinguishable image is formed by the skin marker on the tomographical chart together with the image of the diseased site. Although the skin marker of the invention contains a large quantity of water, it has a shape-retaining property even at 37° C. so that it may be molded to have a desired shape with a rubber-like elasticity to be applied on a desired local position on the surface of a living body while being closely fitted and fixed thereon. The skin marker may be simply fixed in situ by a sticking plaster or a bandage, and the shape and dimensions of the marker may be agreed with those of the diseased site by cutting the peripheral portions thereof by means of scissors, as the shape of the diseased site is progressively diagnosed.

In a case where the material of the invention is used as a skin marker, the rubber-like hydrogel containing a large amount of water may be used directly without any package and any further processing, or a hydrogel having a desired shape may be packed by a polyethylene, polypropylene or nylon film, and the thus packed hydrogel may be used without any additional shaping or may be used after being cut to have pertinent dimensions. Anyway, the material provided by the present invention may be stored stably, and retains the original state containing a large quantity of water for a storage time of more than half year while retaining original NMR imaging properties which clearly differ from those of living tissues when stored in a sealed container.

EXAMPLES OF THE INVENTION

The present invention will now be described with reference to some examples thereof. In the following example, "%" stands for "% by weight".

EXAMPLE 1

Figure 1:
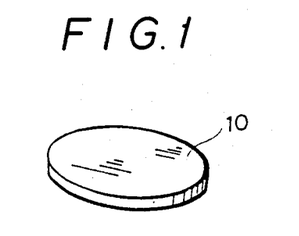
FIG. 1 is a perspective view showing an embodiment of the material for the NMR diagnosis provided by the invention.

An image inspection phantom 10 having the shape as shown in FIG. 1 was prepared.

Into a casting mold for molding a circular disk having a thickness of 1 cm and a diameter of 20 cm, cast was 314g of a 18.6% aqueous solution of a polyvinyl alcohol having an average degree of polymerization of 1,000 and a degree of hydrolysis of 98 mol %. The mold was then cooled to $-30°$ C. to form a frozen mass from which 22g of water was removed under a reduced pressure of 0.1 mmHG. Then, the temperature of the mold was returned back to the room temperature, and the dehydrated mass in the mold was discharged from the mold to obtain a circular disk shape gel having a water content of 80%. The thus prepared gel was stored in a sealed container. The water content of the gel was substantially equivalent to those (ranging from 78 to 81%) of skeletal muscles, small intestine, stomach, uterus and kidney of human body.

The thus prepared circular disk was laid on a horizontal plate having a thickness of 3 mm and made of an acrylic resin, the plate being placed in a static magnetic field (0.15T) of an NMR diagnosis system, and the image thereof was photographed from above along the vertical direction, whereby a substantially perfect circle was imaged and it was found that the thus imaged circle on the display tube or chart had uniform brightness or intensity throughout the whole area thereof.

Then, the uniformity or homogeneousness of the circular disk shape gel had been ascertained by the following experiment. Two samll disks each having a diameter of 7.5 mm and a thickenss or height of 1 cm were cut from randomly selected locations of the circular gel, and charged in a sample tube (Diameter: 7.5 mm) of an NMR spectrometer (0.47T) for microanalysis and the proton density was measured through the 90° pulse method at 37° C., $T_2$ was measured through the spin-echo method and $T_1$ was measured through the inversion recovery method. Similar tests were conducted on ten samples cut from random locations of the circular disk gel including the center and peripheral portions thereof. The result was that all of the ten samples had a water content of 79 to 80%, with $T_1$ value ranging from 0.5 to 0.55 sec. and $T_2$ value ranging from 0.1 to 0.12 sec. The result revealed that the hydrogel provided by the invention is homogenous in regard to the NMR informations. It had thus been ascertained that the NMR diagnosis system which gave correct and uniform image of the homogenous hydrogel disk had been well controlled and adjusted, and that the picturing mechanism which gave uniform image of the 20 cm diameter disk along the vertical imaging direction had also been well controlled and adjusted. The photographing or imaging conditions by the NMR diagnosis system were as follows:

Spin-echo method was used and test was conducted at 37° C.,
Pulse Interval $T_r = 525$ milliseconds,
Echo Time $T_e = 48$ milliseconds.

The aforementioned hydrogel was judged as a material suited for the preparation of a model equivalent to a living tissue in view of the facts that it had dynamic modulus ($10^5$ Nm$^{-2}$) of 0.2 which was comparable to that of KONNYAKU, that it had a stress relaxation (from the room temperature to 37° C.) comparable to that of a silicone rubber in the air atomosphere, and that $\rho$, $T_1$ and $T_2$ thereof were substantially equivalent to those of tissues.

After storing a cut piece of the hydrogel at the room temperature for 150 days while being stored in a sealed container, it was charged again in the same NMR spectrometer (0.47T), and the water content, $T_1$ and $T_2$ thereof were measured at 37° C. to obtain the results that water content was 79%, $T_1 = 0.56$ seconds, and $T_2 = 0.12$ seconds. It had thus been found that the hydrogel provided by the invention were stable with regard to the NMR informations for a period of at least 5 months.

COMPARATIVE EXAMPLE 1

An aqueous solution containing 20% of gelatin was cooled to 0° C. to prepare a gel containing 80% of water. However, the thus prepared gel was easily collapsed at the room temperature and had serious fluidity. Similarly as in Example 1, $T_1$ and $T_2$ of the gel at 37° C. were measured using the same NMR spectrometer to find that $T_1 = 2$ seconds and $T_2 = 1$ second. Those values were considerably different from those of various living tissues, which ranges generally $T_1 =$ about 0.5 second and $T_2 = 0.05$ to 0.1 second.

It was tried to reduce the $T_1$ and $T_2$ values by dissolving nickel chloride hexahydrate in the gelatine solution. However, the $T_1$ value was considerably reduced accompanying with reduction of the $T_2$ value, and it was impossible to simulate the interrelation between the $T_1$ value and the $T_2$ value found in a living body. It was also tried to add graphite together with nickel chloride hexahydrate to reduce the $T_2$ value selectively. However, it was hard to prepare a homogeneous sample, since the graphite powders were gradually sedimented.

With the aim to eliminating the fluidity of the gelatin gel, it was dried to harden the gel by the use of glutaraldehyde or formalin. However, the $T_1$ value of the hardened gel could not be brought to the level of $T_1 = 0.5$ second unless the water content was lowered to not more than 70% with undesirable decrease of $T_2$ (0.2 sec.), leading to the result that a large quantity of graphite had to be added. It was further tried to harden the gel by the addition of aldehyde in the presence of 5,000 to 10,000 ppm of graphite. However, the hardened gel was not homogeneous and could not be molded to have a desired shape.

EXAMPLE 2

Figure 2:
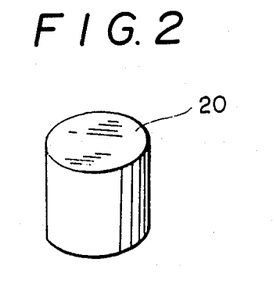
FIG. 2 is a perspective view showing another embodiment of the material for the NMR diagnosis provided by the invention.

A phantom 20 having the shape as shown in FIG. 2 was prepared. A 29% aqueous solution of a polyvinyl alcohol having an average degree of polymerization of 2,000 and a degree of hydrolysis of 99 mol % was cast in a casting mold for molding a cylinder having a diameter of 15 cm and a height of 12 cm, and the cast mass was subjected to repeated freezing and thawing cycles by two times, whereby a hydrogel was prepared. The water content of the hydrogel was 70 to 71%, which was close to those of liver (Water Content: 70 to 77%), Lens (Water Content: 67 to 70%) and prostate (Water Content: 69 to 76%) of human body.

Then, the hydrogel cylinder was placed in the same static magnetic field for the NMR diagnosis as used in Example 1, and about 30 tomographical images, along the horizontal and vertical planes, were photographed at intervals of 3 mm. No distortion of image and no irregularity in imaged pictures were found in both of the horizontal and vertical tomographic photographs. On the other hand, the same cylinder was loaded on a superconducting NMR diagnosis system (1.5T), and the system was operated similarly, whereby distortions of images were found in twenty-three horizontal tomographical photographs at the circumferential portions of the images. It was thus found that the latter-mentioned system had to be re-adjusted.

From the results of measurements of $T_1$ and $T_2$ of the cylindrical hydrogel conducted while using the same NMR spectrometer as used in Example 1, it was ascertained that the values ($T_1 = 0.2$ seconds, $T_2 = 30$ milliseconds) were approximate to the $T_1$ and $T_2$ values of liver.

A cut piece of the cylindrical hydrogel was stored at the room temperature for 180 days in a sealed container, and then charged again in the sample tube of the NMR spectrometer. The results of measurement were that $T_1 = 0.22$ sec., $T_2 = 31$ milliseconds and the water content was 69%. It was thus ascertained that all NMR informations were maintained at constant levels.

COMPARATIVE EXAMPLE 2

Generally following the ordinary method, a polyacrylamide gel was prepared. In detail, 19g of acrylamide, 0.66g of N,N'-methylene-bis-acrylamide and 0.05g of N,N,N'N'-tetramethylethylenediamine were dissolved in 80g of a buffer solution (potassium dihydrogenphosphate/sodium hydrogenphosphate) having a pH value of 7.4. After degassing the solution at the room temperature by reducing the pressure to 20 mmHg, the environmental pressure was returned back to the atmospheric pressure by charging nitrogen stream. While flowing the nitrogen stream, 0.05g of ammonium peroxodisulfate was added to the solution under vigorous agitation to be dissolved in the solution which was then transferred into two test tubes (each having an inner diameter of 23 mm) placed under the nitrogen gas stream atmosphere so that substantially equal quantities of the solution were dividedly poured into the tubes. The contents in the tubes were allowed to stand for an hour, whereby two cylindrical gels each having a diameter of 23 mm and a height of 12 cm were prepared. The bottom of each test tube was cut to open, and then the content therein (gel) was discharged therefrom with care. The gel was fragile and easily broken to be divided into about seven broken pieces during the removal operation conducted using tweezers. The factors of the broken gel were measured at 37° C., while using the same NMR spectrometer as used in Example 1, to obtain the results that the water content was 79%, $T_2 = 1.3$ to 1.45 seconds, and $T_2 = 949$ to 1022 milliseconds. Although the water content of the gel was agreed with those of some living tissues, the $T_1$ value thereof amounted to about three times as high as those of the living tissue and the $T_2$ value thereof amounted to about eleven to twenty times as high as those of the living tissues, as will be apparent from the comparison with the values of uterus (Water Content: 80%, $T_1=0.5$ second, $T_2=50$ milliseconds), the values of gray cerebal tissue and lung (Water Content: 80%, $T_1=0.5$ second, $T_2=90$ milliseconds), the values of ovary (Water Content: 80%, $T_1=0.5$ second, $T_2=60$ milliseconds). With the aim to bringing both of $T_1$ and $T_2$ closer to those of the living tissues, manganese sulfate, nickel chloride hexahydrate and graphite were added to the aqueous solution of acrylamide. However, such trials were not succeeded.

It was judged that the sample gel was inferior in homogeneousness in view of the fact that the values of $T_1$ and $T_2$ were varied at every operations of sampling, charging and measurement. After being stored for 90 days under sealed condition, $T_1$ is reduced to about 1/6 and $T_2$ is reduced to about 1/5 of the initial values. These results show that the stabilities of the gels are not expectable, and that the $T_2$ value is considerably higher than those of living tissues.

EXAMPLE 3

An aqueous solution of a polyvinyl alcohol having an average degree of polymerization of 2,600 and a degree of hydrolysis of 99 mol % was cast in a casting mold for molding a cylinder having a diameter of 30 cm and a height of 30 cm, and the cast mass was frozen at $-40°$ C., followed by thawing, to prepare a hydrogel. The hydrogel had a modulus of elasticity ($10^5$ Nm$^{-2}$) of 0.4 and a hardness resembling that of smooth muscle, and it was judged that the hydrogel had a tentative shape-retaining property. A cut piece of the cylinder was subjected to measurement conducted by using the same NMR spectrometer as used in Example 1. It was found that the water content was 75%, $T=0.4$ sec. and $T_2=60$ milliseconds. The factors were substantially agreed with those of pancreas (Water Content: 75%, $T_1=0.35$ second, $T_2=55$ milliseconds). The cylinder was stored under sealed condition for 180 days, and thereafter the stored sample was subjected to test to obtain the results that the water content was 74.5%, $T_1=0.35$ second and $T_2=60$ milliseconds. The results showed that the NMR informations were maintained stably.

EXAMPLE 4

A skin marker 10 having the shape as shown in FIG. 1 was prepared. 314g of a 18.6% aqueous solution of a polyvinyl alcohol having an average degree of polymerization of 1,000 and a degree of hydrolysis of 98 mol % was cast in a casting mold for molding a circular disk having a thickness of 1 cm and a diameter of 20 cm. The cast mass was then cooled to $-30°$ C. to form a frozen mass from which 22g of water was removed under a reduced pressure of 0.1 mmHg, and then the temperature of the mass was returned back to the room temperature, whereby a circular disk gel having a water content of 80% was prepared. The thus prepared gel was stored in a sealed container. The water content of the gel, as aforementioned, is distinguishably higher than that of living skin (Water Content: 51 to 69%), although it is approximate to those of human internal organs, such as skeletal muscles (Water Content: 79 to 80%), small intestine (Water Content: 80%), stomach (Water Content: 78 to 81%), uterus (Water Content: 80%), lung (Water Content: 80% to 85%), heart (Water Content: 76 to 80%), thymus (Water Content: 76 to 82%), urinary bladder (Water Content: 82%), kidney (Water Content: 76 to 82%), spleen (Water Content: 77%), pancreas (Water Content: 75%), and white cerebal tissue (Water Content: 82 to 84%).

The circular disk was discharged from the sealed container, and then bored by a cork borer to prepare about sixty small disks each having a diameter of about 1 cm which were stored again under sealed condition.

One of the small disks was sterilized with chlorhexidine and then embedded under the back skin of a rabbit After the lapse of 6 months, the surrounding living tissues were inspected to find no foreign body reaction such as inflammation or infiltration of cells and no excessive growth of connective tissue. Likewise, a mongrel dog was intubated under general anesthesia, and the left fourth intercostal space of the dog was cut open for removing a portion of the pericardium (about 1 cm) under controlled respiration, whereby a defect was made and the thin patch (having a thickness of 1 mm) cut from the aforementioned marker was sutured or its defect with Tevdek string. The result of anatomic inspection, after the lapse of one year, revealed that no abnormality was found in the vicinity of the hydrogel prepared by the invention and incorporated in the dog. Similarly, in a case where the same disk was sewn to pleura of a grown dog, no foreign body reaction was found when the operated portion was inspected after the lapse of seven months.

A further experiment was conducted, wherein twenty eyes of 10 rabbits each having a weight of about 2.5 kg were operated such that a bar having a length of 2 cm and a diameter of 2 mm cut from the aforementioned marker was sewn onto the sclera of each eye at a position of in-between the Aequator and ora serrata. After the lapse of one year, the ocules of the twenty eyes were excised from the rabbits and inspected to reveal that no abnormality, such as inflammation or the trace of foreign body reaction, was found on all of the twenty tested ocules. It had been thus judged, in view of the results of the aforementioned animal experiments, that no problems arose when the hydrogel (rubber-like gel containing a large amount of water) of the invention was allowed to contact with living tissues directly.

Supposing the case where a marker is applied at a location through which radioactive ray is irradiated, one of the small hydrogel disk (marker) was applied on the skin of the front breast of a volunteer. An NMR tomographical image was formed under such condition that the images through the marker and through the middle lobe (supposed diseased site) of lung were photographed. The result was that the skin surface per se was not imaged under the conditions that the static magnetic field intensity was 0.15T, the pulse interval was 525 milliseconds and the echo time was 48 milliseconds, whereas both of the middle lobe of lung and the skin marker were clearly imaged. Thus, the positional interrelation betwen the location applied with the skin marker and the middle lobe of lung was determined. Also, the peripheral portions of the marker was cut by scissors to change the shape of the marker and to have a shape of profiling the local site of the middle lobe of lung (supposed diseased site) while repeating the imaging operation to obtain the tomographical images or pictures containing the images of the marker and of the middle lobe.

The aforementioned hydrogel had dynamic modulus ($10^5 Nm^{-2}$) of 0.2 (comparable to that of KON-NYAKU), and it was ascertained that the stress relaxation (within a temperature range of from the room temperature to 37° C.) was comparable to that of a silicone rubber. The results of test for the determination of the NMR properties or characteristics when measured by the use of an NMR spectrometer (0.47T) were that the water content was 80%, that $T_1$ was 0.55 second and that $T_2$ was 0.12 second, all being the values at 37° C. The same small disk (marker) was again measured by the same spectrometer after storing the marker for 6 months under sealed condition to obtain the results that the water content was 79%, $T_1$ was 0.56 second and $T_2$ was 0.11 second. The results showed that the properties of the marker had not been changed during the storage time.

EXAMPLE 5

Figure 3:
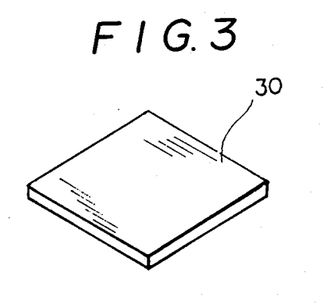
FIG. 3 is a perspective view showing a further embodiment of the material for the NMR diagnosis provided by the invention.

A marker 30 having the shape as shown in FIG. 3 was prepared.

A 15% aqueous solution of a polyvinyl alcohol having an average degree of polymerization of 2,000 and a degree of hydrolysis of 99 mol % was cast into a casting mold for molding a plate having the dimensions of 15 cm×15 cm×0.8 cm. The cast mass was then subjected to two cyclic freezing-and-thawing operations to prepare a hydrogel containing 85% of water. The NMR relaxation times of the thus prepared hydrogel were measured at 37° C. using the same NMR spectrometer as used in Example 1, the result being that $T_1 = 0.7$ second, $T_2 = 200$ milliseconds. It was anticipated, in view of the fact that the concentration of proton and the $T_2$ value were higher than those of the skin of a living body (Water Content: 51 to 69%, $T_1 = 0.5$ second and $T_2 = 45$ millisecondes), that the intensity of the NMR signal emitted therefrom became sufficintly higher. In fact, when a piece having the dimensions of 3 cm×3 cm×0.8 cm was cut from the plate-shape hydrogel and the cut piece was applied on the breast skin, generally in accordance with the operations as described in Example 4, followed by an NMR diagnosis, the following results were obtained. Namely, under a similar imaging condition, the skin surface was not imaged, whereas the skin marker and the middle lobe of lung were clearly imaged to learn the relative positional interrelation between the marker and the middle lobe.

EXAMPLE 6

A 15% aqueous solution of a polyvinyl alcohol having an average degree of polymerization of 2,600 and a degree of hydrolysis of 99 mol % was cast in a mold for molding a circular disk having a diameter of 30 cm and a thickness of 1.3 cm. After freezing the cast mass at −40° C., the frozen mass was thawed to prepare a hydrogel having a dynamic modulus ($10^5 Nm^{-2}$) of 0.15. It was judged that the hydrdgel had tentative shape-retaining property, in view of its dynamic modulus. A cut piece from the hydrogel disk was tested using the same NMR spectrometer as used in Example 1 to obtain the results that the water content was 85%, $T_1$ was 0.7 seconds and $T_2$ was 200 milliseconds. The test results revealed that the hydrogel has a utility for a skin marker similar to that prepared by Example 5, since $T_2$ and the water content thereof were higher than those of the skin of a living body (Water Content: 51 to 69%, $T_1 = 0.5$ second, $T_2 = 45$ milliseconds).

After storing the marker for 180 days under sealed condition, the marker was tested to obtain the results that the water content was 84.5%, $T_1$ was 0.7 second and $T_2$ was 210 milliseconds to reveal the stability of the NMR signals emitted therefrom.

Although the present invention has been described with reference to the specific examples, it should be usually that various modifications and variations can be easily made by those skilled in the art without departing from the spirit of the invention. According, the foregoing disclosure should be interpreted as illustrative only and not to be interpreted in a limiting sense. The present invention is limited only by the scope of the following claims.

What is claimed is:

1. A method of determining positional relationship between a surface of a patient's body and an internal diseased site by nuclear magnetic resonance imaging comprising: (1) applying a hydrogel skin marker to the surface of patient's body and (2) photographing an image of both diseased site and hydrogel skin marker by the nuclear magnetic resonance imaging to thereby determine the positional relationship, said hydrogel skin marker being prepared by a process comprising casting an aqueous solution containing more than 8 wt. % and not more than 50 wt. % of a polyvinyl alcohol having a degree of hydrolysis of not less than 98 mol % and an average polymerization degree of not less than 1000 into a mold having desired shape and dimensions, cooling the cast aqueous solution to a temperature of not higher than minus 10° C. to obtain a cooled frozen mass and thawing the cooled frozen mass or partially dehydrating the cooled mass under vacuum until the percentage dehydration rate reaches not less than 3 wt. %.

2. The method of claim 1 wherein said hydrogel skin marker is cut to have shape and dimensions similar to those of the diseased site by stepwise cutting of peripheral portion of the skin marker during sequential operations of forming cross sectional images thereof together with the formation of the images of the diseased site.

3. The method of claim 1 wherein said hydrogel skin marker contains 80 to 92 wt. % of water.

4. The method of claim 1 wherein said hydrogel skin marker has a shape selected from the group consisting of circular, rectangular and elliptical plates.

5. The method of claim 1 wherein said hydrogel skin marker is cut to have a vacancy hollowed out so as to have a shape simulating the diseased site.

6. The process of claim 1 wherein said cooled mass is thawed.

7. The process of claim 1 wherein said cooled mass is partially dehydrated.

8. The method of claim 1 wherein the content of said polyvinyl alcohol in said aqueous solution is in the range of from more than 8 wt. % to not more than 20 wt. %.

9. A method for adjusting a nuclear magnetic resonance imaging system comprising: (1) placing a hydrogel phantom having a predetermined contour in a static magnetic field of a nuclear magnetic resonance imaging system (2) photographing an image of said hydrogel phantom on display means and (3) adjusting said system until said image has the predetermined contour of said hydrogel phantom and has uniform brightness and intensity throughout the whole area of said image, said hydrogel phantom being prepared by a process comprising casting an aqueous solution containing more than 8 wt. % and not more than 50 wt. % of a polyvinyl alcohol having a degree of hydrolysis of not less than 1000 into a mold having desired shape and dimensions, cooling the cast aqueous solution to a temperature of not higher than minus 10° C. to obtain a cooled frozen mass and thawing the cooled frozen mass or partially dehydrating the cooled mass under vacuum until the percentage dehydration rate reaches no less than 3 wt. %.

10. The method of claim 9 wherein said aqueous solution contains an additional ingredient which does not inhibit gelation of said polyvinyl alcohol in an amount of not more than one-half of the weight of said polyvinyl alcohol contained in said aqueous solution.

11. The method of claim 10 wherein said additional ingredient is selected from the group consisting of isopropyl alcohol, glycerin, propylene glycol, ethyl alcohol, casein, gelatin, albumin, lecithin, monostearin, tristearin, glucose, agar, carrageenan, butyl-p-hydroxybenzoate, phthalocyanine, flavanthrone, nickel salts, copper salts, manganese salts, iron salts, graphite, activated carbon, silica-alumina, zeolite, calcium silicate and mixtures thereof.

12. The method of claim 9 wherein said hydrogel phantom contains 50 92 wt. % of water.

13. The method of clam 9 wherein said aqueous solution of said polyvinyl alcohol further contains a lipid.

14. The method of claim 9 wherein said aqueous solution of said polyvinyl alcohol is heated to a temperature of not lower than 70° C. and then a solid lipid which has been heated to be liquefied is added.

15. The method of claim 9 wherein a plurality of said hydrogel phantoms having different water contents are joined together.

16. The method of claim 9 wherein the contour of said hydrogel phantom is selected from the group consisting of circular, elliptical, spherical, annular, cylindrical and tubular shapes and strips.

17. The process of claim 9 wherein said cooled mass is thawed.

18. The process of claim 9 wherein said cooled mass is partially dehydrated.

* * * * *

UNITED STATES PATENT AND TRADEMARK OFFICE
CERTIFICATE OF CORRECTION

PATENT NO.   : 4,774,957

DATED        : October 4, 1988

INVENTOR(S)  : Masao Nambu; Hitoshi Goshima

It is certified that error appears in the above-identified patent and that said Letters Patent is hereby corrected as shown below:

Column 20, line 4 "phantom contains 5092" should be
--phantom contains 50 to 92--.

Signed and Sealed this

Fourth Day of April, 1989

Attest:

DONALD J. QUIGG

*Attesting Officer*         *Commissioner of Patents and Trademarks*